(12) United States Patent
Morales

(10) Patent No.: US 6,167,605 B1
(45) Date of Patent: Jan. 2, 2001

(54) COLLET TYPE CRIMPING TOOL

(75) Inventor: Stephen A. Morales, Mountain View, CA (US)

(73) Assignee: Advanced Cardiovascular Systems, Inc., Santa Clara, CA (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/928,877

(22) Filed: Sep. 12, 1997

(51) Int. Cl.[7] .................................................. B21D 39/04

(52) U.S. Cl. ................ 29/282; 29/283.5; 606/1; 606/198; 623/1

(58) Field of Search ............................ 29/283.5, 243.522, 29/234, 235, 243.519, 237, 243.5, 243.518, 515, 282; 279/42; 72/402; 606/1, 108, 198; 623/1

(56) References Cited

U.S. PATENT DOCUMENTS

| | | | |
|---|---|---|---|
| 141,992 | * | 8/1873 | Carr . |
| 579,214 | * | 3/1897 | Adams . |
| 852,290 | * | 4/1907 | Neal . |
| 915,184 | * | 3/1909 | Keirn . |
| 1,045,886 | * | 12/1912 | Reay . |
| 1,230,561 | * | 6/1917 | Chige . |
| 1,268,171 | * | 6/1918 | Spaulding . |
| 1,758,261 | * | 5/1930 | Leland . |
| 2,465,433 | * | 3/1949 | Doniger . |
| 3,496,684 | * | 2/1970 | Banning et al. . |
| 3,898,897 | | 8/1975 | Jauhiainen . |
| 4,107,964 | * | 8/1978 | Smith . |
| 4,215,871 | * | 8/1980 | Hirsch et al. . |
| 4,907,336 | | 3/1990 | Gianturco . |
| 4,987,722 | * | 1/1991 | Koebbeman . |
| 5,026,377 | * | 6/1991 | Burton et al. ........................ 606/108 |
| 5,132,066 | | 7/1992 | Charlesworth et al. . |
| 5,133,732 | | 7/1992 | Wiktor . |
| 5,183,085 | | 2/1993 | Timmermans . |
| 5,540,124 | | 7/1996 | Srhoj . |
| 5,546,646 | | 8/1996 | Williams et al. . |
| 5,626,604 | | 5/1997 | Cottone, Jr. . |
| 5,630,830 | | 5/1997 | Verbeek . |
| 5,736,251 | * | 4/1998 | Pinchuck ............................. 428/447 |
| 5,810,873 | * | 9/1998 | Morales .............................. 606/198 |
| 5,893,867 | * | 4/1999 | Burton et al. ........................ 606/108 |

FOREIGN PATENT DOCUMENTS

WO 97 09946   3/1997  (WO) .

OTHER PUBLICATIONS

*The eXTraordinary Stent*, C.R. Bard Brochure (Undated).

* cited by examiner

Primary Examiner—S. Thomas Hughes
Assistant Examiner—Jermie E. Cozart
(74) Attorney, Agent, or Firm—Fulwider Patton Lee & Utecht, LLP

(57) ABSTRACT

A sterile tool for crimping a stent onto a balloon catheter is disclosed. The stent crimping tool includes two major components, a cylindrical body having external threads and a rotating collar with internal threads engaging the external threads. The collet end of the cylindrical body is split into segmented jaws that are biased to flare outward in an open state. A stent loaded onto a balloon catheter and situated inside the open segmented jaws can undergo a crimping operation when the collar is rotated and advances toward the flared open segmented jaws. When the collar engages the segmented jaws, the jaws are forced to converge and close onto the stent-catheter assembly thereby crimping the stent onto the balloon catheter.

16 Claims, 2 Drawing Sheets

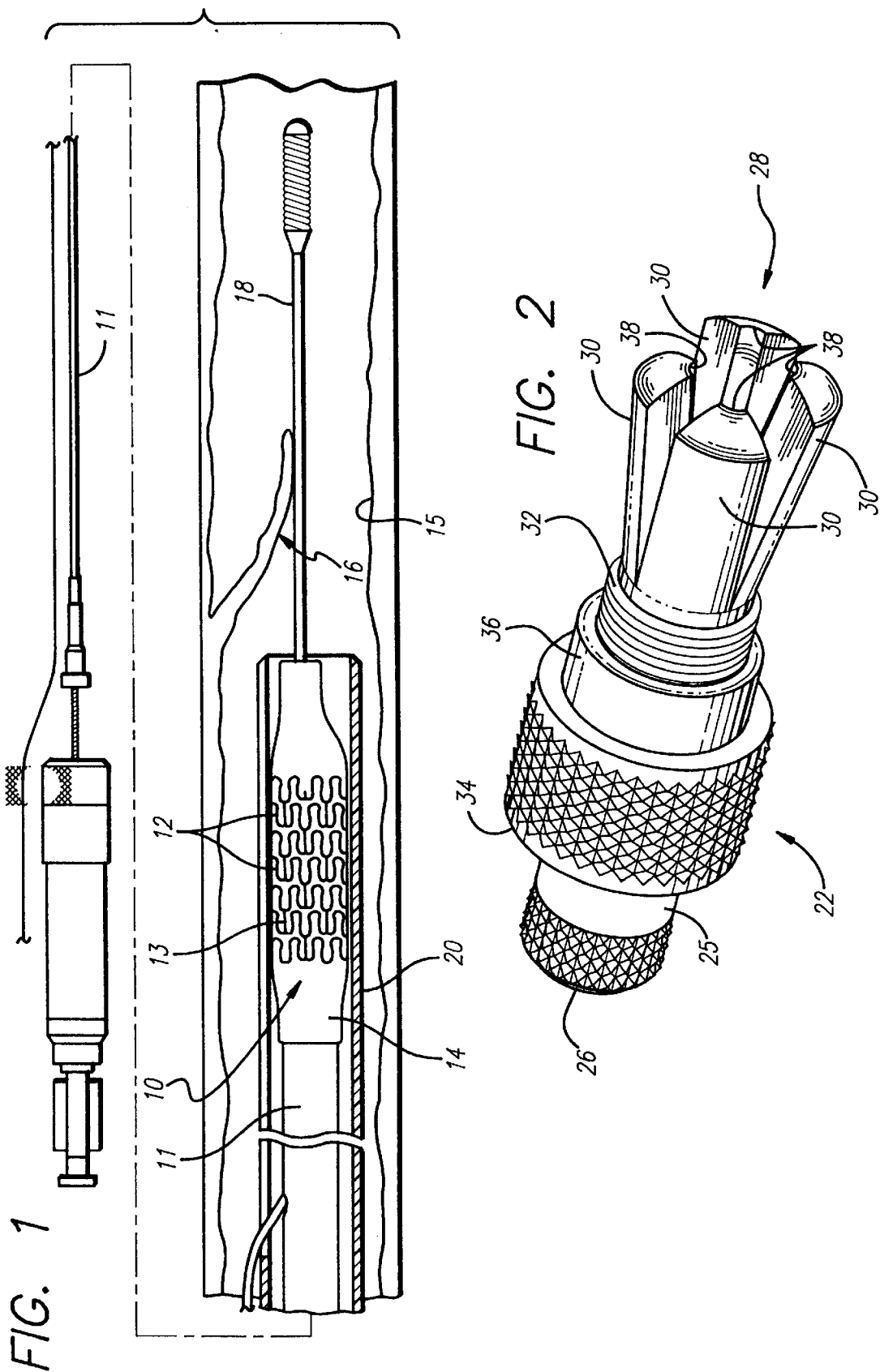

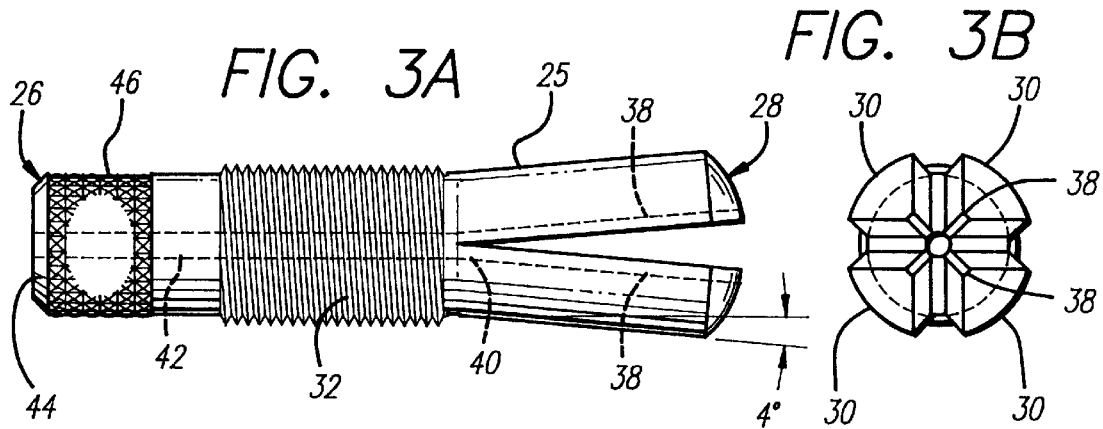
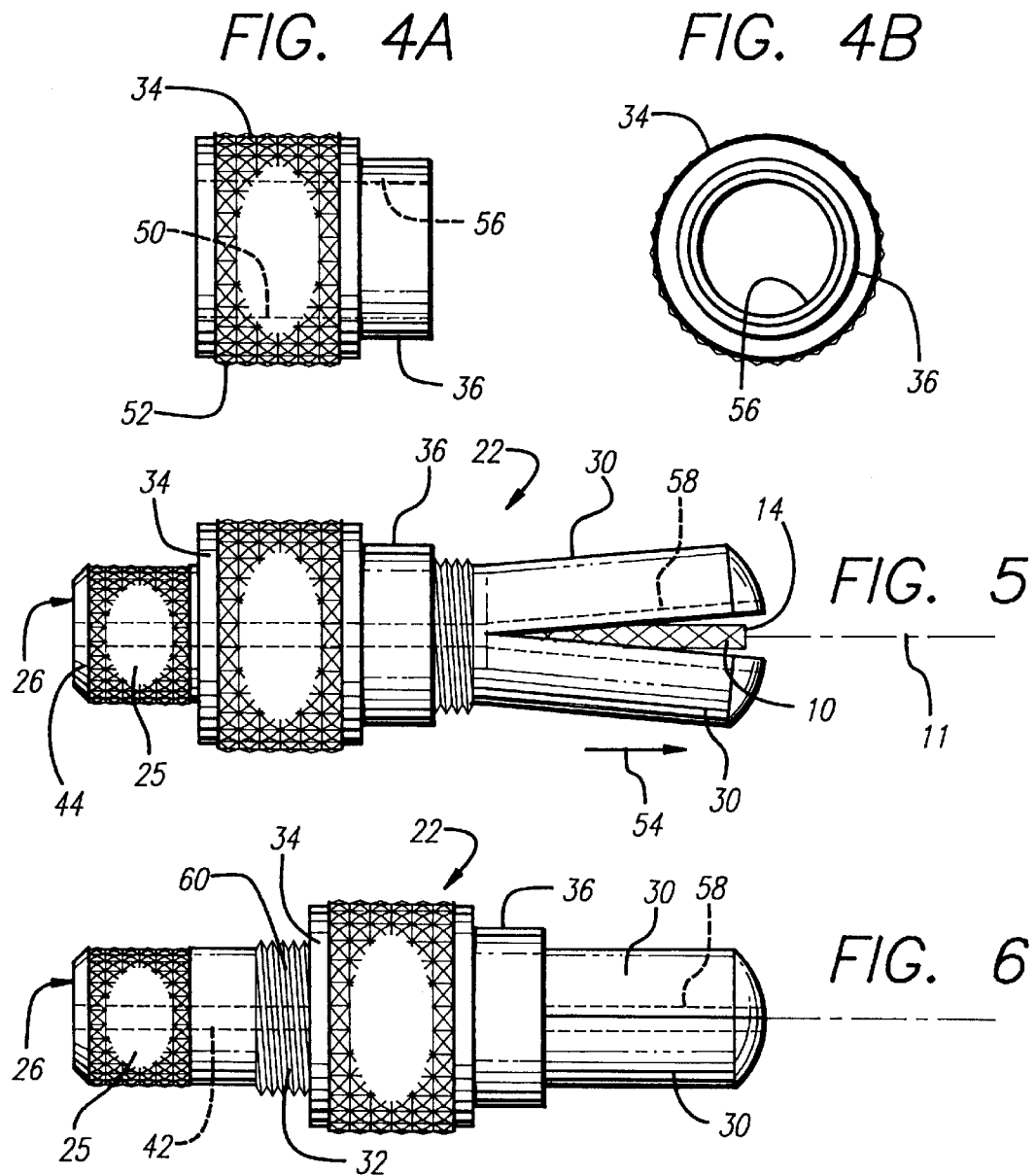

COLLET TYPE CRIMPING TOOL

BACKGROUND OF THE INVENTION

The present invention relates to an apparatus for loading a tubular graft, such as a stent, onto the distal end of a catheter assembly of the kind used, for example, in percutaneous transluminal coronary angioplasty (PTCA) procedures, in percutaneous transluminal angioplasty (PTA) procedures, atherectomies, and the like.

In typical PTCA procedures, a guiding catheter is percutaneously introduced into the cardiovascular system of a patient, through the brachial or femoral arteries and advanced through the vasculature until the distal end of the guiding catheter is in the ostium of the aorta leading to the coronary arteries. A guide wire and a dilatation catheter having a balloon on the distal end are introduced through the guiding catheter with the guide wire sliding within the dilatation catheter. The guide wire is first advanced out of the guiding catheter into the patient's coronary vasculature and the dilatation catheter is advanced over the previously advanced guide wire until the dilatation balloon is properly positioned across the arterial lesion. Once in position across the lesion, a flexible and expandable balloon is inflated to a predetermined size with a radiopaque liquid at relatively high pressures to radially compress the atherosclerotic plaque of the lesion against the inside of the artery wall and thereby dilate the lumen of the artery. The balloon is then deflated to a small profile so that the dilatation catheter can be withdrawn from the patient's vasculature and the blood flow resumed through the dilated artery. As should be appreciated by those skilled in the art, while the above-described procedure is typical, it is not the only method used in angioplasty.

In angioplasty procedures of the kind referenced above, restenosis of the artery may develop at or near the treatment area, which may require another angioplasty procedure, a surgical bypass operation, or some other method of repairing or strengthening the area. To reduce the likelihood of the development of restenosis and to strengthen the area, a physician can implant an intravascular prosthesis for maintaining vascular patency, commonly known as a stent, inside the artery at the treated area. The stent is transported in its delivery diameter through the patient's vasculature. At the deployment site, the stent is expanded to a larger diameter, often by inflating the balloon portion of the catheter. The stent also may be of the self-expanding type.

Since the catheter and stent travel through the patient's vasculature, and typically through the coronary arteries, the stent must have a small delivery diameter and must be firmly attached to the catheter until the physician is ready to implant it. Thus, the stent must be loaded onto the catheter so that it does not interfere with delivery, and it must not come off the catheter until it is implanted.

In procedures where the stent is placed over the balloon portion of the catheter, it is necessary to crimp the stent onto the balloon portion to reduce its diameter and to prevent it from sliding off the catheter when the catheter is advanced through the patient's vasculature. Non-uniform crimping can result in sharp edges being formed along the now uneven surface of the crimped stent. Furthermore, non-uniform stent crimping may not achieve the desired minimal profile for the stent and catheter assembly. Where the stent is not reliably crimped onto the catheter, the stent may slide off the catheter and into the patient's vasculature prematurely as a loose foreign body, possibly causing blood clots in the vasculature, including thrombosis. Therefore, it is important to ensure the proper crimping of a stent onto a catheter in a uniform and reliable manner.

This crimping is often done by hand, which can be unsatisfactory due to the uneven application of force resulting in non-uniform crimps. In addition, it is difficult to visually judge when a uniform and reliable crimp has been applied.

Some self-expanding stents are difficult to load by hand onto a delivery device such as a catheter. Furthermore, the more the stent is handled the higher the likelihood of human error, which would be antithetical to a properly crimped stent. Accordingly, there is a need in the art for a device for reliably crimping a stent onto a catheter.

There have been attempts at devising a tool for crimping a stent onto a balloon delivery catheter. An example of such a tool comprises a series of plates having substantially flat and parallel surfaces that move in a rectilinear fashion with respect to each other. A stent carrying catheter is disposed between these surfaces, which surfaces crimp the stent onto the outside of the catheter by their relative motion and applied pressure. The plates have multiple degrees of freedom and may have force-indicating transducers to measure and indicate the force applied to the catheter during crimping of the stent.

Another stent loading tool design is comprised of a tubular member housing a bladder. The tubular member and bladder are constructed to hold a stent that is to be crimped onto a balloon catheter assembly. Upon placement of the stent over the balloon portion of the catheter, a valve in the loading tool is activated to inflate the bladder. The bladder compresses the stent radially inward to a reduced diameter onto the balloon portion of the catheter to achieve a snug fit. In this way, the stent is crimped onto the distal end of a balloon catheter with a minimum of human handling. The foregoing stent crimping tools are disclosed in, for example, commonly owned and assigned U.S. Pat. Nos. 5,437,083 and 5,546,646 to Williams et al.

Yet another stent crimping tool is known in the art as the BARD XT, which is actually a stent loader. It is constructed of a tubular body with a ball at one end connected to a plurality of long, thin strips passing through the rigid tubular body. An uncrimped stent is placed over the plurality of long, thin strips, which hold the stent in an expanded state. The balloon portion of a catheter is inserted into the cylindrical space formed by the plurality of strips. When the user pulls on the ball while holding the tubular body against the stent, the strips are slid from beneath the stent and the stent is transferred onto the balloon portion.

Still another conventional stent crimping tool is manufactured by JOHNSON & JOHNSON and appears similar to a hinged nutcracker. Specifically, the tool is comprised of two hand operated levers hinged at one end and gripped in the palm of the hand at the opposite end. A cylindrical opening holding a crimping tube is provided through the mid-portion of the tool to receive therein a stent loaded onto a balloon catheter. The crimping operation is performed by the user squeezing the handle thereby pressing the crimping tube which in turn pinches the stent onto the balloon catheter.

While the prior art devices are suitable for crimping stents onto balloon catheters, they suffer from problems such as non-uniform crimping forces, resulting in non-uniform crimps, and they are unsuitable for use by physicians in a cath lab who desire to crimp the stent onto the balloon catheter.

SUMMARY OF THE INVENTION

The present invention is directed to a method and apparatus for crimping an intravascular stent onto the distal end of a catheter. The apparatus is comprised of a cylindrical body having a gripping end and a collet end, wherein the cylindrical body at the collet end transitions into a plurality of segmented jaws that are flared outward. Threads are disposed on the cylindrical body in between the collet end and the gripping end. A collar is rotatably mounted on the cylindrical body and has an internal threaded opening engaging the threads on the body and a front inside diameter of the internal threaded opening that engages the plurality of segmented jaws, wherein advancing the collar along the threads translates the front inside diameter over the flared segmented jaws to converge the jaws into a closed state.

In a preferred embodiment, a groove is formed along a length of each jaw so that when the plurality of segmented jaws are in the closed state, the grooves collectively form a cylindrical cavity leading to an opening at the collet end of the cylindrical body. Thus, closing the segmented jaws onto the stent mounted to the balloon portion of the catheter when the stent and catheter are situated within the cavity crimps the stent onto the catheter.

In the preferred embodiment, the present invention crimping apparatus has four segmented jaws and each segmented jaw includes a generally quarter-circle, cross-sectional shape. The segmented jaws may be modified with a liner, various coatings, foam plates, or a floating head. Such modifications are aimed at gripping and holding the stent without damaging the part. Moreover, when the converged segmented jaws in the closed state are lined, the lining material ensures a constant diameter crimp. The diameter can be adjusted by changing the thicknesses or shapes of the lining material.

In the preferred embodiment of the present invention, the tool is designed to be used in a cath lab to crimp intravascular stents onto balloon catheters by forcing the stent to compress from four points around its circumference onto the exterior diameter of the balloon. The balloon with the uncrimped stent mounted in the correct position thereon is placed inside the flared collet end of the cylindrical body with the collar threaded thereon half way toward the flared collet end.

The balloon and stent are held in position by a third party, a table, or other support. While the balloon and stent are supported, another person can twist the collar to advance it along the length of the threads thereby forcing the segmented jaws at the collet end to converge and close down on to the stent. This closing action crimps the stent onto the balloon.

As mentioned earlier, grooves are formed along the length of each jaw so that in their closed state, the grooves collectively form a cylindrical cavity the dimensions and shape of which match the crimped stent and contain the crimped stent and the catheter balloon when the segmented jaws have fully converged. The grooves may be profiled to vary the diameter and contours along the length of the crimped stent. Some resistance should be encountered, but is normal to the compression process. The stent and catheter balloon can be released from the tool by unscrewing the collar from the cylindrical body thereby releasing the external pressure on the converged segmented jaws allowing the jaws to open.

If the crimping process is not satisfactory, the process can be repeated for as many times as the user would wish. The tool and the operation thereof are extremely simple and repeatable. Indeed, with the rotating motion of the collar along the cylindrical body, it is possible to mark the tool for the precise distance the collar is advanced along the threads of the cylindrical body for accurate crimping of the stent by the converging segmented jaws.

The present invention thus provides the end user with a precise and repeatable method of crimping a stent onto a balloon catheter. To achieve precision, the present invention may be modified with an optional micrometer, strain gauges, or the like for tight control. In contrast, many conventional processes are unreliable and achieve inconsistent and non-uniform crimps. Furthermore, the present invention crimping tool can be used with any stent that is released without a delivery system. The crimping tool may also be sold alone. Finally, the present invention tool solves a common problem with conventional tools of not being able to crimp down to any exact diameter. These and other advantages of the present invention will become more apparent from the following detailed description when taken in conjunction with the accompanying drawings.

BRIEF DESCRIPTION OF THE DRAWINGS

FIG. 1 is an elevational view, partially in section, depicting an intravascular stent that is mounted on a delivery balloon catheter and disposed within a vessel.

FIG. 2 is a perspective view of a preferred embodiment of the present invention crimping tool showing the segmented jaws in the open state.

FIGS. 3A and 3B show a side elevational and a front view, respectively, of a preferred embodiment cylindrical body having a gripping end and a flared collet end with the segmented jaws in the flared open state.

FIGS. 4A and 4B depict a side elevational and a front view, respectively, of a preferred embodiment collar having internal threads, a leading edge, and a knurled exterior.

FIG. 5 is a side elevational view of the present invention wherein a catheter-stent assembly has been loaded into the collet end just prior to the crimping operation.

FIG. 6 is a side elevational view of the present invention crimping tool shown in FIG. 5, wherein the crimping operation has occurred and the segmented jaws have converged onto the stent-catheter assembly due to advancement of the collar along the cylindrical body of the crimping tool.

DETAILED DESCRIPTION OF THE PREFERRED EMBODIMENTS

FIG. 1 illustrates intravascular stent 10 which is mounted onto delivery catheter 11. Stent 10 generally comprises a plurality of radially expandable cylindrical elements 12 disposed generally coaxially and interconnected by members 13 disposed between adjacent cylindrical elements 12. Delivery catheter 11 has an expandable portion or balloon 14 for expanding stent 10 within artery 15 or other vessel. Artery 15, as shown in FIG. 1, has dissected lining 16 which has occluded a portion of the arterial passageway.

Delivery catheter 11, onto which stent 10 is mounted, can be essentially the same as a conventional balloon dilatation catheter for angioplasty procedures. Balloon 14 may be formed of suitable materials such as polyethylene, polyvinyl chloride, polyethylene terephthalate and other like polymers. In order for stent 10 to remain in place on balloon 14 during delivery to the site of the damage within artery 15, stent 10 is compressed onto balloon 14. This compressing step is known as crimping.

An optional retractable protective delivery sleeve or sheath 20 may be provided to further ensure that stent 10 stays in place on balloon 14 of delivery catheter 11 and to prevent abrasion of the body lumen by the open surface of stent 10 during delivery to the desired arterial location. Other means for securing stent 10 onto balloon 14 may also be used, such as providing collars or ridges on the ends of the working portion, i.e., the cylindrical portion of balloon 14.

The catheter-stent assembly can be introduced into the patient's vasculature through processes known in the art, generally immediately after PTCA, PTA, or atherectomy procedures. Briefly, guide wire 18 is disposed across the treated arterial section, referred to as target area 16, and the catheter-stent assembly is advanced over guide wire 18 within artery 15 until stent 10 is directly under target area 16. Prior to inflation of balloon 14, delivery sleeve 20 is retracted to expose stent 10. Balloon 14 of delivery catheter 11 is then expanded using an inflation fluid. Expansion of balloon 14 in turn expands stent 10 into contact with artery 15. Next, balloon 14 is deflated and catheter 11 is withdrawn leaving stent 10 to support the target area 16. As mentioned above, in order to ensure proper seating of stent 10 on balloon 14, and to ensure proper deployment of stent 10 at target area 16 within artery 15, the stent crimping procedure is highly critical.

In order to implant stent 10 in a vessel, it is first mounted onto inflatable balloon 14 on the distal extremity of delivery catheter 11. Stent 10 is crimped down onto balloon 14 to ensure a low profile. The present invention addresses this crimping procedure.

FIG. 2 provides a perspective view of a preferred embodiment of the present invention stent crimping tool 22. In the preferred embodiment shown, stent crimping tool 22 is comprised of cylindrical body 25 having gripping end 26 opposed to collet end 28. Collet end 28 is comprised of a plurality of flared open segmented jaws 30 formed by splitting collet end 28 into discrete branches.

Cylindrical body 25 further includes external threads 32 disposed in between gripping end 26 and collet end 28. The present invention stent crimping tool 22 further includes rotating cylindrical collar 34 having internal threads that engage external threads 32 of cylindrical body 24. Cylindrical collar 34 also includes leading edge 36 designed to engage segmented jaws 30 as collar 34 is advanced forward toward collet end 28. As this engagement progresses, leading edge 36 forces segmented jaws 30 from their flared open state into a closed state in which all segmented jaws 30 converge toward a theoretical axial center line of cylindrical body 24. FIG. 2 further illustrates optional groove 38 preferably formed into each segmented jaw 30 that extends the length of each jaw 30.

As best seen in FIGS. 3A and 3B, which provide a side elevational view and a front view, respectively, of a preferred embodiment of cylindrical body 24, groove 38 transitions at confluence point 40 into bore 42 extending the length of cylindrical body 24. Gripping end 26 may be optionally knurled to provide a better gripping surface. Other finishing methods known in the art can be used to enhance the friction at this point as well.

Cylindrical body 24 preferably is approximately 3.75 inches long, however, this length can vary depending upon the application. At gripping end 26, the edges are chamfered 44 and as mentioned earlier, a section of cylindrical body 24 just beyond chamfer 44 is knurled for better gripping. Just beyond knurled portion 46 are external threads 32 which in the preferred embodiment are a 5 degree coarse thread. External threads 32 wind to approximately 2.5 inches up the shaft of cylindrical body 24. Then the profile of cylindrical body 24 flares out at a preferable 4 degree angle from its center axis, and transitions into collet end 28. Collet end 28 is not only flared out but is also split down the shaft 2.5 inches where the threads begin, approximately coinciding with confluence point 40. The split is preferably a 4 degree taper that begins at the 2.5 inches mark from gripping end 26 and expands at 4 degrees relative to the center axis to collet end 28, creating an approximate 0.189 inch gap between the ends of cylindrical body 24.

In this embodiment, collet end 28 is split into preferably four discrete segmented jaws 30 and each segmented jaw 30 flares outward at an approximate 4 degree angle relative to the axial center line of cylindrical body 24. Segmented jaws 30 are preferably formed from four quarter-tube sections defined by a small inner radius of 0.007 inch. In their flared open state, the outside diameter of flared open segmented jaws 30 is approximately 1.205 inch contrasted with the preferably 1 inch diameter of the unflared section of cylindrical body 24. Groove 38 formed in each segmented jaw 30 is best seen in the front view of cylindrical body 24 in FIG. 3B.

FIGS. 4A and 4B provide a side elevational view and a front view, respectively, of cylindrical collar 34 that is rotatably mounted to cylindrical body 24. In the preferred embodiment shown in FIGS. 4A and 4B, cylindrical collar 34 has a generally cylindrical shape with a first diameter, and has leading edge 36 with a smaller second diameter. Therefore, as seen in the side elevational view of FIG. 4A, cylindrical collar 34 preferably has a step down diameter. Cylindrical collar 34 is thus a two-stage cylinder that in the preferred embodiment is approximately 1.5 inch in length with a maximum diameter of 2 inches. The inner diameter is a constant at 1 inch, and is tapped with a 5 degree coarse internal thread 50 to match external threads 32 on cylindrical body 24. The large diameter section of cylindrical collar 34 is preferably 1 inch in length and has a 2 inch diameter, and is further chamfered on both edges. This section also is knurled 52 to facilitate a better grip on the part.

Leading edge 36 has a 0.5 inch length and is cut down in diameter to preferably 1.5 inch. Leading edge 36 is significant in forcing the flared outward segmented jaws 30 from the open state into the closed state in which each segmented jaw 30 converges toward the axial center line of cylindrical body 24.

FIGS. 5 and 6 are side elevational views of a preferred embodiment of the present invention stent crimping tool 22. In FIG. 5, segmented jaws 30 are flared open to receive balloon catheter 11 with stent 10 loaded onto balloon 14. The stent-balloon catheter assembly are shown in FIG. 5 situated within a space or cavity 58 formed by segmented jaws 30 in their flared open state.

As mentioned earlier, the present invention stent crimping tool 22 is designed to be used in a cath lab to crimp stents onto the balloon portion of catheters by compressing the stent onto the balloon from preferably four points around its outer circumference. Therefore, as seen in FIG. 5, balloon 14, with the uncrimped stent mounted in the correct position, is placed inside collet end 28 of cylindrical body 24. At this stage, cylindrical collar 34 has already been threaded halfway toward collet end 28, preferably 1.5 inch as measured from the back edge of gripping end 26. The stent-catheter assembly can be advanced in through either method until it is aligned in the collet segments.

In the cath lab, ideally, the stent-catheter assembly is held in position by a third party, a table, or other support known in the art. While the stent-catheter assembly is supported, another person can twist cylindrical collar 34 thereby advancing collar 34 along cylindrical body 24 in the direction of arrow 54.

In this motion, leading edge 36 is translated into engagement with segmented jaws 30. The preferably smooth inside diameter 56 of cylindrical collar 34 slides over the flared open segmented jaws 30. As cylindrical collar 34 is advanced farther in the direction of arrow 54, inside diameter 56 engages and forces segmented jaws 30 from their open state to converge toward an axial center line of cylindrical body 24 into a closed state. The convergence of segmented jaws 30 into the stent-catheter assembly compresses stent 10 onto balloon 14.

Cavity 58 is formed when segmented jaws 30 converge and completely engage the stent-catheter assembly. Cavity 58 is partially formed by the collective convergence of grooves 38. FIG. 6 shows this condition in which segmented jaws 30 have assumed their closed state and cylindrical collar 34 has been advanced fully forward on cylindrical body 24. As seen in FIG. 6, bore 42 is needed to accommodate longer catheters in which the balloon sits farther back.

The stent-catheter assembly can be released by unscrewing cylindrical collar 34 from cylindrical body 24. This action disengages leading edge 36 from contact with segmented jaws 30 which are preferably biased to flare outward. Segmented jaws 30 then return to their flared open state thus releasing the stent-catheter assembly permitting removal thereof.

If the crimp is not satisfactory, the present invention process can be repeated for as many times as necessary to achieve a tight, uniform crimp. As seen here, the operation of stent crimping tool 22 is simple, repeatable, and can be controlled precisely. In fact, with the rotating motion of cylindrical collar 34, it is possible to mark cylindrical body 24 to indicate the amount of forward advancement translating to the amount of convergence in segmented jaws 30 thereby accurately crimping stent 10. To ensure accuracy, FIG. 6 depicts optional indicator mark 60 to help the user control the amount of advancement of cylindrical collar 34 and the associated amount of convergence of segmented jaws 30 during the crimping operation.

As will be appreciated by those skilled in the art, the present invention stent crimping tool 22 is designed both for single use applications in a cath lab by a physician, or for multiple use applications in a sterile environment in a high volume manufacturing facility. In the manufacturing facility where sterile conditions exist, stent crimping tool 22 can be used repeatedly to crimp stents onto balloon catheters until the mechanism wears out. Thus, repeated uses of the present invention are contemplated for controlled, sterile environments although single use applications are required when used by cath lab personnel.

The present invention stent crimping tool can be used with any stent that is released without a delivery system. The crimping tool may also be sold alone because its design is robust enough to undergo many uses. The present invention crimping tool 22 can be used to crimp any expandable stent onto any catheter, and is particularly suitable for stents implanted in the coronary arteries, arteries, veins, and other body lumens, and also is suitable to crimp saphenous vein grafts.

In a preferred embodiment, all parts of stent crimping tool 22 are made from machined polymers. On the other hand, the present invention is also well suited to be made from surgical steel, aluminum, or other metals, where it can be used and reused.

In an alternative embodiment, the grooves of the segmented jaws and the jaws themselves can be coated with rubber or other resilient materials. In addition, in other alternative embodiments, the grooves and/or the segmented jaws can include floating heads, foam plates, or a lining in order to effect a desired outside diameter or a specific profile for the stent. For the same effect, a lining may also be used to cover the stent and catheter prior to crimping.

The split in cylindrical body 24 at collet end 28 can be achieved by using a band saw or rotating blade type tool wherein the natural reaction of the polymer base material is to bias the segmented jaws outward into a flared configuration. It is also possible through processes known in the art to heat treat the polymer to create the outward bias of the flared segmented jaws.

Other modifications can be made to the present invention without departing from the scope thereof. The specific dimensions, procedural steps, and materials of construction are provided as examples, and substitutes are readily contemplated which do not depart from the invention.

What is claimed is:

1. A combination tool for crimping a stent onto a catheter and the stent, the combination comprising:

the tool having a cylindrical body having a gripping end and a collet end, wherein the cylindrical body at the collet end transitions into a plurality of segmented jaws that are flared outward to receive the stent therein;

external threads disposed on the cylindrical body in between the collet end and the gripping end;

a collar rotatably mounted on the cylindrical body having an internal threaded opening engaging the external threads on the body and a front inside diameter of the internal threaded opening engages the plurality of segmented jaws;

wherein advancing the collar along the threads translates the front inside diameter over the segmented jaws to converge the segmented jaws into a closed state; and a groove formed along a length of each jaw engaging the stent, wherein when the plurality of segmented jaws are in the closed state, the grooves collectively form a cylindrical cavity leading to an opening at the collet end of the cylindrical body;

whereby closing the segmented jaws onto the stent mounted on the catheter, when the stent and catheter are situated within the cavity, crimps the stent onto the catheter.

2. The combination according to claim 1, wherein the tool includes four segmented jaws and each segmented jaw includes a generally quarter-tubular wall cross-sectional shape.

3. The combination according to claim 1, wherein the groove formed along each segmented jaw includes a lining.

4. The combination according to claim 1, wherein the collar includes an annular cross-sectional shape.

5. The combination according to claim 1, wherein the collar includes a segment that has a smooth inside diameter.

6. The combination according to claim 1, wherein the cylindrical body includes a metallic material.

7. The combination according to claim 1, wherein the collet end is rounded.

8. The combination according to claim 1, wherein the segmented jaws include a coating of material on at least a portion thereof.

9. The combination according to claim 1, wherein the plurality of segmented jaws of the cylindrical body include a polymer.

10. A combination tool for crimping a stent onto a catheter and the stent, the combination comprising:
- the tool having a cylindrical body having a gripping end and a collet end, wherein the collet end includes a plurality of segmented jaws having a flared open state and a converged closed state;
- an opening in the collet end leading to a cavity receiving the stent therein formed collectively by the plurality of segmented jaws in the converged closed state;
- external threads disposed on the cylindrical body;
- a collar having an internal opening with internal threads, wherein the collar is rotatably disposed on the body with the internal threads engaging the external threads on the body;
- wherein the segmented jaws are biased to flare outward toward the open state and the collar overcomes the bias when it is advanced along the external threads to partially engage the segmented jaws and to converge the segmented jaws together into the closed state to engage the stent held therein; and
- whereby converging the segmented jaws on the stent positioned on the catheter located within the cavity crimps the stent onto the catheter.

11. The combination according to claim 10, wherein the cavity has a cylindrical shape, and the cavity extends along an axial length of the cylindrical body.

12. The combination according to claim 10, wherein at least one of the segmented jaws includes a coating on at least a portion thereof.

13. The combination according to claim 10, wherein the collet end includes a tubular cross-sectional shape.

14. The combination according to claim 10, wherein each segmented jaw in the flared open state defines at least a four degree angle from a longitudinal axis of the cylindrical body.

15. The combination according to claim 10, wherein the collar includes a cylindrical shape having an overall diameter with a step-down profile defining a leading edge having a diameter smaller than the overall diameter of the collar, and wherein the leading edge is proximal to and engages the segmented jaws to converge the segmented jaws into the closed state as the collar is advanced along the external threads of the body.

16. The combination according to claim 10, wherein the cavity is configured to receive a balloon portion of a catheter.

* * * * *